United States Patent
Wen (10) Patent No.: US 8,684,729 B2
(45) Date of Patent: Apr. 1, 2014

(54) DISPOSABLE DENTAL ALIGNER

(75) Inventor: Huafeng Wen, Redwood City, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 11/074,298

(22) Filed: Mar. 7, 2005

(65) Prior Publication Data
US 2006/0199140 A1    Sep. 7, 2006

(51) Int. Cl.
*A61C 3/00*        (2006.01)

(52) U.S. Cl.
USPC ......................................................... 433/24

(58) Field of Classification Search
USPC ............... 433/24, 18, 215–225, 6–7; 705/2–3
See application file for complete search history.

(56) References Cited

U.S. PATENT DOCUMENTS

| | | | |
|---|---|---|---|
| 4,360,341 A * | 11/1982 | Dellinger | 433/24 |
| 4,755,139 A | 7/1988 | Abbatte | |
| 4,798,534 A | 1/1989 | Breads | |
| 4,856,991 A | 8/1989 | Breads | |
| 4,936,862 A | 6/1990 | Walker | |
| 5,011,405 A | 4/1991 | Lemchen | |
| 5,035,613 A | 7/1991 | Breads | |
| 5,049,075 A * | 9/1991 | Barrut | 433/196 |
| 5,055,039 A | 10/1991 | Abbatte | |
| 5,059,118 A | 10/1991 | Breads | |
| 5,186,623 A | 2/1993 | Breads | |
| 5,273,429 A | 12/1993 | Rekow | |
| 5,338,198 A | 8/1994 | Wu | |
| 5,340,309 A | 8/1994 | Robertson | |
| 5,342,202 A | 8/1994 | Deshayes | |
| 5,368,478 A | 11/1994 | Andreiko | |
| 5,382,164 A | 1/1995 | Stern | |
| 5,452,219 A | 9/1995 | Dehoff | |
| 5,549,476 A | 8/1996 | Stern | |
| 5,587,912 A | 12/1996 | Andersson | |
| 5,607,305 A | 3/1997 | Andersson | |
| 5,645,421 A | 7/1997 | Slootsky | |
| 5,879,158 A | 3/1999 | Doyle | |
| 5,975,893 A | 11/1999 | Chishti | |
| 6,217,325 B1 | 4/2001 | Chishti | |
| 6,227,850 B1 | 5/2001 | Chishti | |
| 6,227,851 B1 | 5/2001 | Chishti | |
| 6,299,440 B1 | 10/2001 | Phan | |
| 6,309,215 B1 | 10/2001 | Phan | |
| 6,454,565 B2 * | 9/2002 | Phan et al. | 433/6 |
| 6,497,574 B1 | 12/2002 | Miller | |
| 6,499,997 B2 | 12/2002 | Chishti | |
| 6,514,074 B1 | 2/2003 | Chishti | |
| 6,524,101 B1 | 2/2003 | Phan | |
| 6,554,611 B2 | 4/2003 | Chishti | |
| 6,572,372 B1 | 6/2003 | Phan | |
| 6,582,227 B2 | 6/2003 | Phan | |
| 6,582,229 B1 | 6/2003 | Miller | |

(Continued)

*Primary Examiner* — Yogesh Patel
(74) *Attorney, Agent, or Firm* — Wilson Sonsini Goodrich & Rosati (57) ABSTRACT

A method for treating a patient's teeth includes determining an initial configuration of the patient's teeth, determining a final configuration of the patient's teeth, designing a movement path for at least one of the patient's teeth from the initial configuration to the final configuration, dividing the movement path into a plurality of successive treatment steps, each having a target configuration for the patient's teeth, and producing two or more dental aligners of substantially identical shape for at least one of the treatment steps in accordance with the target configuration.

21 Claims, 3 Drawing Sheets

(56) References Cited

U.S. PATENT DOCUMENTS

| | | |
|---|---|---|
| 6,602,070 B2 | 8/2003 | Miller |
| 6,607,382 B1 | 8/2003 | Kuo |
| 6,621,491 B1 | 9/2003 | Baumrind |
| 6,626,666 B2 | 9/2003 | Chishti |
| 6,629,840 B2 | 10/2003 | Chishti |
| 6,633,789 B1 | 10/2003 | Nikolskiy |
| 6,665,570 B2 | 12/2003 | Pavloskaia |
| 6,682,346 B2 | 1/2004 | Chishti |
| 6,685,469 B2 | 2/2004 | Chishti |
| 6,685,470 B2 | 2/2004 | Chishti |
| 6,688,886 B2 | 2/2004 | Hughes |
| 6,699,037 B2 | 3/2004 | Chishti |
| 6,705,861 B2 | 3/2004 | Chishti |
| 6,722,880 B2 * | 4/2004 | Chishti et al. .................. 433/24 |
| 6,726,478 B1 | 4/2004 | Isiderio |
| 6,729,876 B2 | 5/2004 | Chishti |
| 2002/0163096 A1* | 11/2002 | Price .................. 264/16 |
| 2002/0187451 A1* | 12/2002 | Phan et al. ........................ 433/6 |
| 2003/0075186 A1* | 4/2003 | Florman ...................... 128/869 |
| 2003/0207224 A1* | 11/2003 | Lotte .................................. 433/6 |
| 2004/0142299 A1* | 7/2004 | Miller ............................. 433/24 |
| 2004/0214914 A1* | 10/2004 | Marmo ......................... 523/106 |

\* cited by examiner

DISPOSABLE DENTAL ALIGNER

CROSS-REFERENCES TO RELATED INVENTIONS

The present invention is also related to concurrently filed (Mar. 7, 2005) and commonly assigned U.S. patent application Ser. No. 11/074,299, entitled "Producing Physical Dental Arch Model Having Individually Adjustable Tooth Models" by Liu et al., U.S. patent application Ser. No. 11/074,301, entitled "Dental Aligner for Providing Accurate Dental Treatment" by Liu et al., U.S. patent application Ser. No. 11/074,297, entitled "Producing Wrinkled Dental Aligner for Dental Treatment" by Liu et al., and U.S. patent application Ser. No. 11/074,300, entitled "Fluid Permeable Dental Aligner" by Huafeng Wen.

The present invention is also related to commonly assigned U.S. patent application Ser. No. 10/979,823, titled "Method and apparatus for manufacturing and constructing a physical dental arch model" by Huafeng Wen, filed Nov. 2, 2004, U.S. patent application Ser. No. 10/979,497, titled "Method and apparatus for manufacturing and constructing a dental aligner" by Huafeng Wen, filed Nov. 2, 2004, U.S. patent application Ser. No. 10/979,504, titled "Producing an adjustable physical dental arch model" by Huafeng Wen, filed Nov. 2, 2004, and U.S. patent application Ser. No. 10/979,824, titled "Producing a base for physical dental arch model" by Huafeng Wen, filed Nov. 2, 2004. The disclosure of these related applications are incorporated herein by reference.

The present invention is also related to commonly assigned U.S. patent application Ser. No. 11/013,152, titled "A base for physical dental arch model" by Huafeng Wen, filed Dec. 14, 2004, commonly assigned U.S. patent application Ser. No. 11/012,924, titled "Accurately producing a base for physical dental arch model" by Huafeng Wen, filed Dec. 14, 2004, commonly assigned U.S. patent application Ser. No. 11/013,145, titled "Fabricating a base compatible with physical dental tooth models" by Huafeng Wen, filed Dec. 14, 2004, commonly assigned U.S. patent application Ser. No. 11/013,156, titled "Producing non-interfering tooth models on a base" by Huafeng Wen, filed Dec. 14, 2004, commonly assigned U.S. patent application Ser. No. 11/013,160, titled "System and methods for casting physical tooth model" by Huafeng Wen, filed Dec. 14, 2004, commonly assigned U.S. patent application Ser. No. 11/013,159, titled "Producing a base for accurately receiving dental tooth models" by Huafeng Wen, and filed Dec. 14, 2004, commonly assigned U.S. patent application Ser. No. 11/013,157, titled "Producing accurate base for dental arch model" by Huafeng Wen, filed Dec. 14, 2004. The disclosure of these related applications are incorporated herein by reference.

TECHNICAL FIELD

This application generally relates to the field of dental care, and more particularly to the field of orthodontics.

BACKGROUND

Orthodontics is the practice of manipulating a patient's teeth to provide better function and appearance. In general, brackets are bonded to a patient's teeth and coupled together with an arched wire. The combination of the brackets and wire provide a force on the teeth causing them to move. Once the teeth have moved to a desired location and are held in a place for a certain period of time, the body adapts bone and tissue to maintain the teeth in the desired location. To further assist in retaining the teeth in the desired location, a patient may be fitted with a retainer.

To achieve tooth movement, orthodontists utilize their expertise to first determine a three-dimensional mental image of the patient's physical orthodontic structure and a three-dimensional mental image of a desired physical orthodontic structure for the patient, which may be assisted through the use of x-rays and/or models. Based on these mental images, the orthodontist further relies on his/her expertise to place the brackets and/or bands on the teeth and to manually bend (i.e., shape) wire, such that a force is asserted on the teeth to reposition the teeth into the desired physical orthodontic structure. As the teeth move towards the desired location, the orthodontist makes continual judgments as to the progress of the treatment, the next step in the treatment (e.g., new bend in the wire, reposition or replace brackets, is head gear required, etc.), and the success of the previous step.

In general, the orthodontist makes manual adjustments to the wire and/or replaces or repositions brackets based on his or her expert opinion. Unfortunately, in the oral environment, it is difficult for a human being to accurately develop a visual three-dimensional image of an orthodontic structure due to the limitations of human sight and the physical structure of a human mouth. In addition, it is difficult to accurately estimate three-dimensional wire bends (with an accuracy within a few degrees) and to manually apply such bends to a wire. Further, it is difficult to determine an ideal bracket location to achieve the desired orthodontic structure based on the mental images. It is also difficult to manually place brackets in what is estimated to be the ideal location. Accordingly, orthodontic treatment is an iterative process requiring multiple wire changes, with the process success and speed being very much dependent on the orthodontist's motor skills and diagnostic expertise. As a result of multiple wire changes, patient discomfort is increased as well as the cost. As one would expect, the quality of care varies greatly from orthodontist to orthodontist as does the time to treat a patient.

As described, the practice of orthodontic is very much an art, relying on the expert opinions and judgments of the orthodontist. In an effort to shift the practice of orthodontic from an art to a science, many innovations have been developed. For example, U.S. Pat. No. 5,518,397 issued to Andreiko, et. al. provides a method of forming an orthodontic brace. Such a method includes obtaining a model of the teeth of a patient's mouth and a prescription of desired positioning of such teeth. The contour of the teeth of the patient's mouth is determined, from the model. Calculations of the contour and the desired positioning of the patient's teeth are then made to determine the geometry (e.g., grooves or slots) to be provided. Custom brackets including a special geometry are then created for receiving an arch wire to form an orthodontic brace system. Such geometry is intended to provide for the disposition of the arched wire on the bracket in a progressive curvature in a horizontal plane and a substantially linear configuration in a vertical plane. The geometry of the brackets is altered, (e.g., by cutting grooves into the brackets at individual positions and angles and with particular depth) in accordance with such calculations of the bracket geometry. In such a system, the brackets are customized to provide three-dimensional movement of the teeth, once the wire, which has a two dimensional shape (i.e., linear shape in the vertical plane and curvature in the horizontal plane), is applied to the brackets.

Other innovations relating to bracket and bracket placements have also been patented. For example, such patent innovations are disclosed in U.S. Pat. No. 5,618,716 entitled "Orthodontic Bracket and Ligature" a method of ligating arch wires to brackets, U.S. Pat. No. 5,011,405 "Entitled Method for Determining Orthodontic Bracket Placement," U.S. Pat. No. 5,395,238 entitled "Method of Forming Orthodontic Brace," and U.S. Pat. No. 5,533,895 entitled "Orthodontic Appliance and Group Standardize Brackets therefore and methods of making, assembling and using appliance to straighten teeth".

Kuroda et al. (1996) Am. J. Orthodontics 110:365-369 describes a method for laser scanning a plaster dental cast to produce a digital image of the cast. See also U.S. Pat. No. 5,605,459. U.S. Pat. Nos. 5,533,895; 5,474,448; 5,454,717; 5,447,432; 5,431,562; 5,395,238; 5,368,478; and 5,139,419, assigned to Ormco Corporation, describe methods for manipulating digital images of teeth for designing orthodontic appliances.

U.S. Pat. No. 5,011,405 describes a method for digitally imaging a tooth and determining optimum bracket positioning for orthodontic treatment. Laser scanning of a molded tooth to produce a three-dimensional model is described in U.S. Pat. No. 5,338,198. U.S. Pat. No. 5,452,219 describes a method for laser scanning a tooth model and milling a tooth mold. Digital computer manipulation of tooth contours is described in U.S. Pat. Nos. 5,607,305 and 5,587,912. Computerized digital imaging of the arch is described in U.S. Pat. Nos. 5,342,202 and 5,340,309.

Other patents of interest include U.S. Pat. Nos. 5,549,476; 5,382,164; 5,273,429; 4,936,862; 3,860,803; 3,660,900; 5,645,421; 5,055,039; 4,798,534; 4,856,991; 5,035,613; 5,059,118; 5,186,623; and 4,755,139.

The key to efficiency in treatment and maximum quality in results is a realistic simulation of the treatment process. Today's orthodontists have the possibility of taking plaster models of the upper and lower arch, cutting the model into single tooth models and sticking these tooth models into a wax bed, lining them up in the desired position, the so-called set-up. This approach allows for reaching a perfect occlusion without any guessing. The next step is to bond a bracket at every tooth model. This would tell the orthodontist the geometry of the wire to run through the bracket slots to receive exactly this result. The next step involves the transfer of the bracket position to the original malocclusion model. To make sure that the brackets will be bonded at exactly this position at the real patient's teeth, small templates for every tooth would have to be fabricated that fit over the bracket and a relevant part of the tooth and allow for reliable placement of the bracket on the patient's teeth. To increase efficiency of the bonding process, another option would be to place each single bracket onto a model of the malocclusion and then fabricate one single transfer tray per arch that covers all brackets and relevant portions of every tooth. Using such a transfer tray guarantees a very quick and yet precise bonding using indirect bonding.

U.S. Pat. No. 5,431,562 to Andreiko et al. describes a computerized, appliance-driven approach to orthodontics. In this method, first certain shape information of teeth is acquired. A uniplanar target arcform is calculated from the shape information. The shape of customized bracket slots, the bracket base, and the shape of the orthodontic archwire, are calculated in accordance with a mathematically-derived target archform. The goal of the Andreiko et al. method is to give more predictability, standardization, and certainty to orthodontics by replacing the human element in orthodontic appliance design with a deterministic, mathematical computation of a target archform and appliance design. Hence the '562 patent teaches away from an interactive, computer-based system in which the orthodontist remains fully involved in patient diagnosis, appliance design, and treatment planning and monitoring.

More recently, Align Technology, Inc. began offering transparent, removable aligning devices as a new treatment modality in orthodontics. In this system, an impression model of the dentition of the patient is obtained by the orthodontist and shipped to a remote appliance manufacturing center, where it is scanned with a CT scanner. A computer model of the dentition in a target situation is generated at the appliance manufacturing center and made available for viewing to the orthodontist over the Internet. The orthodontist indicates changes they wish to make to individual tooth positions. A revised virtual model is provided for the orthodontist to review, until the target situation is agreed upon. A series of removable aligning devices or shells are manufactured and delivered to the orthodontist. The shells will move the patient's teeth to the desired or target position.

U.S. Pat. No. 6,699,037 describes improved methods and systems for repositioning teeth from an initial tooth arrangement to a final tooth arrangement. Repositioning is accomplished with a system comprising a series of appliances configured to receive the teeth in a cavity and incrementally reposition individual teeth in a series of successive steps, usually including at least four successive steps, often including at least ten steps, sometimes including at least twenty-five steps, and occasionally including forty or more steps. Most often, the methods and systems will reposition teeth in from ten to twenty-five successive steps, although complex cases involving many of the patient's teeth may take forty or more steps. The successive use of a number of such appliances permits each appliance to be configured to move individual teeth in small increments, typically less than 2 mm, preferably less than 1 mm, and more preferably less than 0.5 mm. These values refer to the maximum linear translation of any point on a tooth as a result of using a single appliance. The movements provided by successive appliances, of course, will usually not be the same for any particular tooth. Thus, one point on a tooth may be moved by a different distance as a result of the use of one appliance and thereafter moved by a different distance and/or in a different direction by a later appliance.

The individual appliances preferably comprise a polymeric shell having the teeth-receiving cavity formed therein, typically by molding. Each individual appliance is configured so that its tooth-receiving cavity has a geometry corresponding to an intermediate or end tooth arrangement intended for that appliance. That is, when an appliance is first worn by the patient, certain of the teeth will be misaligned relative to an undeformed geometry of the appliance cavity. The appliance, however, is sufficiently resilient to accommodate or conform to the misaligned teeth, and will apply sufficient resilient force against such misaligned teeth in order to reposition the teeth to the intermediate or end arrangement desired for that treatment step.

The fabrication of aligners using a stereo lithography process is disclosed in U.S. Pat. Nos. 6,471,511 and 6,682,346. The stereo lithography process builds the aligner layer by layer, and may use a different aligner mold at each stage of the treatment. There is therefore a long felt need for practical, effective and efficient methods to produce a dental aligner.

Other long recognized issues with the dental aligners include the loss of function due relaxation of the dental aligner over time, inconvenience, and oral hygiene problems. The conventional aligners often become relaxed and open up after repeated usage by a patient. The dental aligner tends to bend outwards when a patient bites the aligner. The repeated removal and wearing of the aligner can also cause the bottom part of the aligner to expand. The deformation results in a loss of corrective force to be applied to the patient's teeth by the aligner device and insufficient or inaccurate teeth movement in the orthodontic treatment. The corrective measures can also be costly.

Conventional aligners can be inconvenient to use. Damage and loss of dental aligners is the major cause for reordering and remaking of the dental aligners. The conventional dental aligners require special care by the patient: the aligners are required to be kept in a cool and dry place and in special containers to prevent them from being damaged. The dental aligners need to be handled with care to avoid damages which can be caused by for example sharp fingernails. Another cause of relaxation is the inherent properties of the material. The patient is also recommended not to drink hot beverages because the aligner material is often sensitive to excessive heat.

The patient's oral hygiene can also be compromised. The aligners can retain an unpleasant appearance from smoking, or become dirty and catch permanent stains from the food or drinks. It is recommended that the conventional dental aligners should be removed before eating, drinking, and smoking, which is often inconvenient and impractical.

SUMMARY OF THE INVENTION

The present invention has been devised to substantially eliminate the foregoing problems and is to provide methods and apparatus to manufacture and construct the physical dental arch model. Implementations of the system may include one or more of the following.

In one aspect, the present invention relates to a method for treating a patient's teeth, comprising
determining an initial configuration of the patient's teeth;
determining a final configuration of the patient's teeth;
designing a movement path for at least one of the patient's teeth from the initial configuration to the final configuration;
dividing the movement path into a plurality of successive treatment steps, each having a target configuration for the patient's teeth; and
producing two or more dental aligners of substantially identical shape for at least one of the treatment steps in accordance with the target configuration.

In another aspect, the present invention relates to a method for treating a patient's teeth, comprising
determining a target configuration for the patient's teeth;
producing two dental aligners having substantially identical shape; and
using the two dental aligners to move the patient's teeth to the target configuration.

In yet another aspect, the present invention relates to a system for treating a patient's teeth, comprising:
a computer configured to determine a target configuration for the patient's teeth; and
an apparatus configured to produce two dental aligners configured to move the patient's teeth to the target configuration, wherein the two dental aligners have substantially identical shape.

Embodiments may include one or more of the following advantages. The present invention provides convenient dental aligning devices for patients. The dental aligners provided are disposable. Redundant dental aligners are provided to the patient at each treatment step. If a dental aligner is lost or damaged, the patient does not have to request to remake another aligner and wait for it to be made and sent to her. Special care needed for the traditional dental aligners are no longer needed. The disclosed disposable dental aligners are therefore more convenient for patients to use. The costs are also reduced for re-ordering and remaking lost or damaged dental aligners.

Another advantage of the present invention is that it provides more accurate and effective dental treatment for the patients. The conventional dental aligners often relax over the use of a period of time and lose their strength to exert intended forces on the patients' teeth, which results in ineffective and inaccurate movements for the dental treatment. In the present invention, multiple dental aligners disclosed are provided at each treatment step. The dental aligners can be disposed before they become relaxed. The accuracy and effectiveness of the dental treatment are therefore improved. As a result, the overall treatment time and cost can be reduced.

Yet another advantage of the present invention is that it improves the patient's oral hygiene by allowing the patient to frequently replace the dental aligner worn by a short period of time by new dental aligner.

The details of one or more embodiments are set forth in the accompanying drawing and in the description below. Other features, objects, and advantages of the invention will become apparent from the description and drawings, and from the claims.

BRIEF DESCRIPTION OF THE DRAWINGS

The accompanying drawing, which are incorporated in and form a part of this specification, illustrate embodiments of the invention and, together with the description, serve to explain the principles of the invention.

DETAILED DESCRIPTION OF EMBODIMENTS

Systems and methods are provided to overcome a long recognized issue with dental aligners. The aligners are made of plastic materials and can often become relaxed and open up after repeated usage by a patient. The patient can bite the aligner, causing the aligner to bend outwards. Each time the patient takes off the aligner during eating, thinking, or before sleep, the bottom part of the aligner tends to open up and relax. Furthermore, the material relaxation at the bottom of the aligner, due to usage over time, can render ineffective the application of force at the bottom of the teeth. The relaxation of the aligner can occur in as short a period as a few days of usage. The loss of corrective force applied by the aligner to the patient's teeth results in insufficient or inaccurate teeth movement. The corrective measures can include reordering of the same aligners and delay in the orthodontic treatment, which are costly for the patients.

Figure 1A:
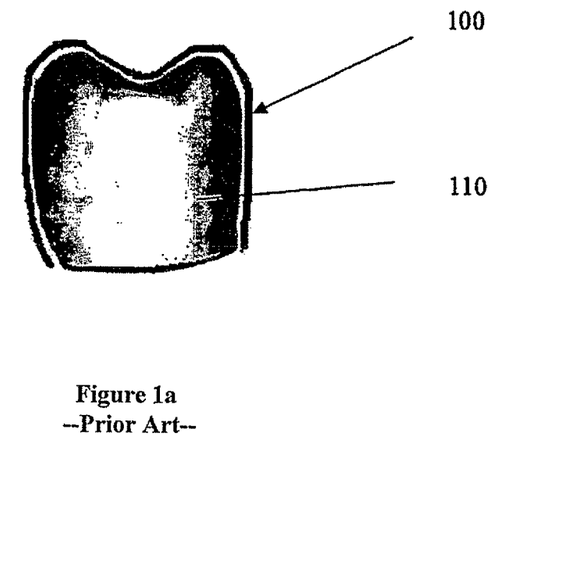
FIG. 1a illustrates the side view of a new conventional dental aligner worn on a patient's tooth.
Figure 1B:
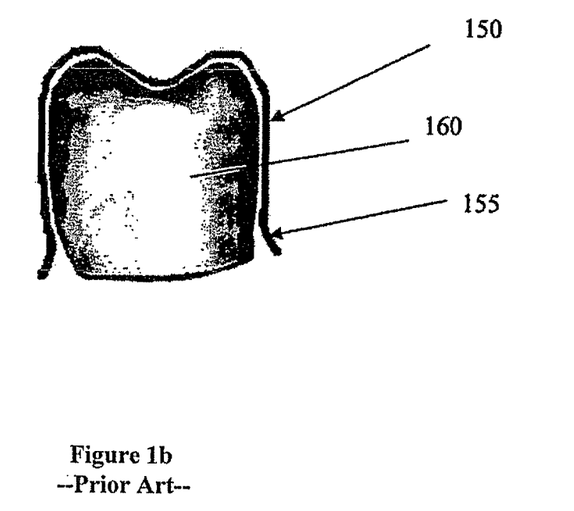
FIG. 1b shows the side view of a conventional dental aligner worn after a period of usage.
Figure 2:
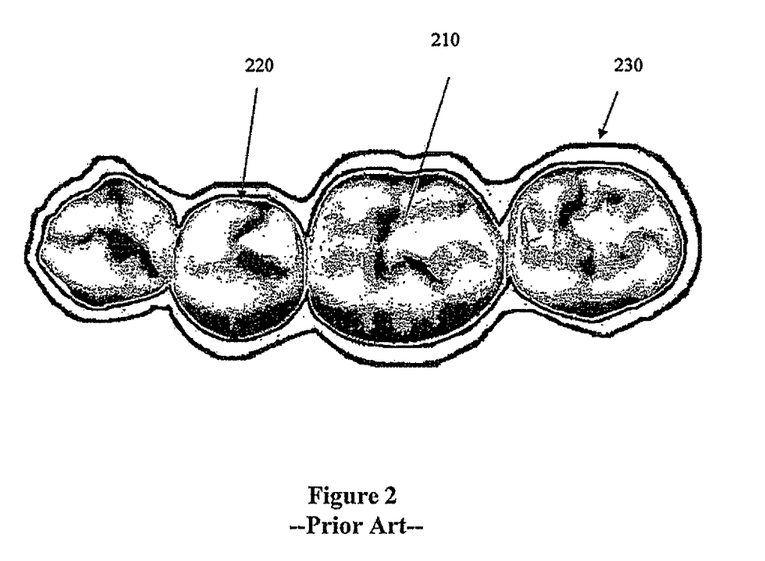
FIG. 2 illustrates the top views of a conventional dental aligner when it is newly worn and after it is worn for a period of time.

To illustrate the above described problem, FIG. 1a illustrates a side view of a new aligner 100 worn a patient's tooth 110. The aligner is typically in a shell shape, comprising shell portion, a tip portion, and a bottom portion. The inner surface of the shell portion is to be in contact with the patient's teeth. The aligner fits properly at the bottom of the tooth where the gingival separates the tooth from the root. The newly worn aligner 100 provides proper and effective force for the tooth movement in the orthodontic treatment. FIG. 1b shows the side view of the aligner 150 that has been worn on the patient's tooth 160 after a period of usage such as a few days or a week. The lower part 155 of the dental aligner 150 is relaxed and opened up, which prevents the dental aligner 150 to exert proper stress on the bottom of the tooth. The dental aligner 150 thus can no longer produce effective and accurate tooth movement. FIG. 2 illustrates the top view of a conventional dental aligner 220 that is newly worn on a patient's tooth 210. After it is worn for a period of time, the dental aligner 230 is relaxed and loose. It can no longer apply effective forces to the tooth 210.

Figure 3:
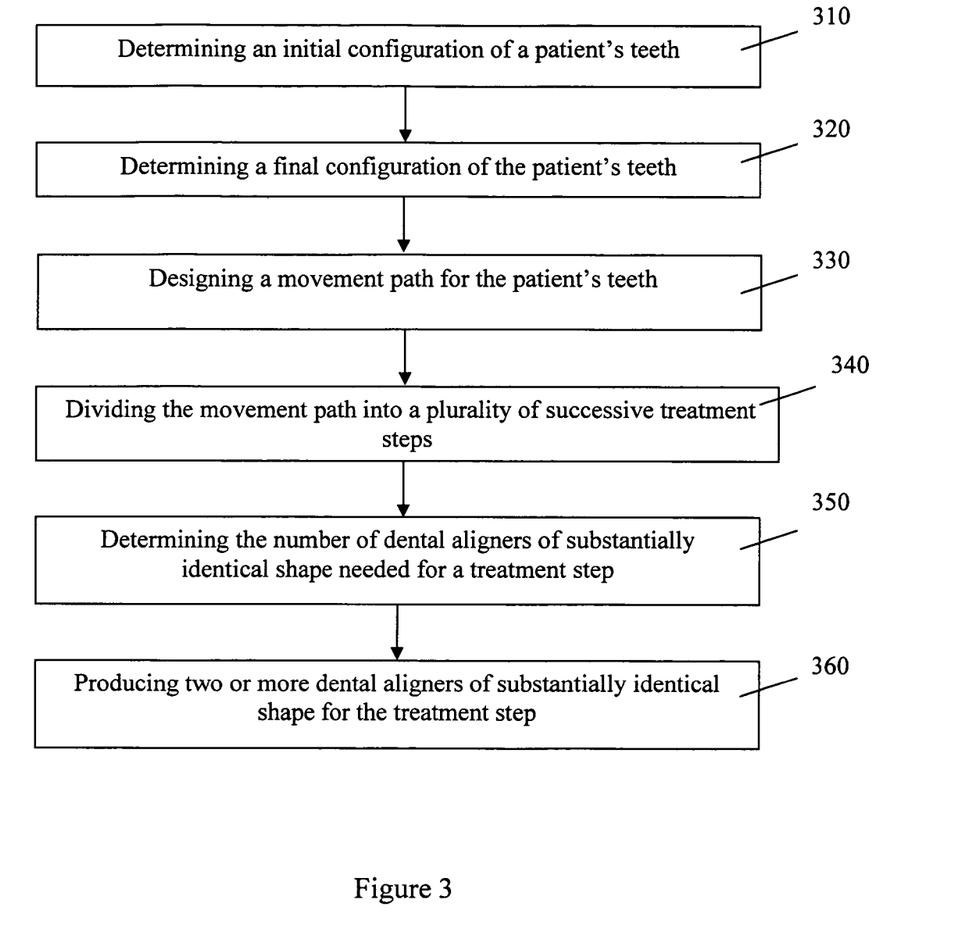
FIG. 3 illustrates a process for producing a disposable dental aligner.

FIG. 3 illustrates a process for producing a disposable dental aligner. In an orthodontic treatment, an initial configuration of the patient's arch is first determined in step 310. The patient's arch can include one or more teeth in the upper jaw and lower jaw. The configuration includes positions and orientations of the patient's teeth. The initial configuration can be obtained by first producing a negative impression of the patient's arch and then scanning the surfaces of the negative impression by 3D positional measurement devices. The dentist analyzes the initial configuration of the patient's teeth and determines the final configuration of the patient's teeth in step 320. The final configuration comprises the positions and the orientations of the patient's teeth after the corrective treatment.

The dentist will then design a movement path for each of the teeth involved in step 330. A typical orthodontic treatment is usually divided into a plurality of successive treatment steps in step 340. One or more specifically designed disposable dental aligners are used to move the patient's teeth to a pre-designed target configuration. The treatment at the step is intended to produce incremental amounts of changes in positions or orientations that are within the comfort tolerance of the patient as well as the performance of the dental aligner.

In accordance with the present invention, a plurality of disposable dental aligners is designed for each step of the treatment. The plurality of disposable dental aligners has substantially identical shape designed to achieve the same incremental teeth movement at that particular step. The patient will receive the set of disposable dental aligners all at once; and he or she may switch from one disposable dental aligner to another without visiting the dentist office.

The disposable dental aligners are designed to be worn by the patient for a shorter period of time than conventional dental aligners. A patient can change his or her disposable dental aligner every week, every three days, every day, or even in a matter of hours or minutes. For example, the patient can wear a disposable aligner just for having dinner.

The frequency of change of the disposable dental aligner may depend on the patient's profile or life style. The number of disposable dental aligners for each treatment step is determined in step 350, which can depend on factors such as the number of meals, the sleeping pattern, and dental hygiene of the particular patient. For example, if a person is a heavy smoker, he will be advised to change the disposable aligners more frequently than someone who is very strict about his oral hygiene. The number of disposable dental aligners for each treatment step can also depend on the relative magnitude of the incremental movement designed in that treatment step.

The effect of the disposable dental aligners can be simulated by computer modeling. The progressive teeth configurations in an orthodontic treatment can be represented by a digital dental arch model. The disposable aligners can be simulated by a digital aligner model. The effects of the multiple disposable dental aligners on the patient's teeth can be simulated at each treatment step. The computer simulation helps to determine the number of steps needed for each treatment, the material properties of the disposable dental aligners as well as the number of dental aligners of substantially identical shape for each step.

The use of multiple disposable dental aligners allows a disposable disposal dental aligner to be replaced before it is relaxed and deforms. This assures the uniform application of force on the patient's teeth over time and improves the accuracy of treatment. Because of their effectiveness, the disposable dental aligners can shorten the overall treatment time. Disposable dental aligners are also more comfortable for the patient to wear because of the smaller granular movements induced by each disposable dental aligner.

The disposable aligners are produced in step 360 for each treatment step. Two or more disposable dental aligners can be molded using the same mold in a casting chamber. The mold can be a negative impression produced by a physical dental arch model that comprises the patient's tooth models that are configured in the target configuration for the specific treatment step. The disposable dental aligners can also be fabricated by a CNC based machine that receives a digital aligner model as input.

Details of producing physical dental arch model and associated base are disclosed in the above referenced and commonly assigned U.S. patent application Ser. No. 10/979,823, titled "Method and apparatus for manufacturing and constructing a physical dental arch model" by Huafeng Wen, filed Nov. 2, 2004, U.S. patent application Ser. No. 10/979,497, titled "Method and apparatus for manufacturing and constructing a dental aligner" by Huafeng Wen, filed Nov. 2, 2004, U.S. patent application Ser. No. 10/979,504, titled "Producing an adjustable physical dental arch model" by Huafeng Wen, filed Nov. 2, 2004, and U.S. patent application Ser. No. 10/979,824, titled "Producing a base for physical dental arch model" by Huafeng Wen, filed Nov. 2, 2004. The disclosure of these related applications are incorporated herein by reference.

The disposable dental aligners produced by the above processes therefore have substantially the same shape. As described above, different materials however can be used for the different molding events to mold disposable aligners of different hardness. The surface of the positive impression can include features for molding wrinkled surfaces to produce the wrinkled disposable aligners. Details of wrinkled dental aligners and the fabrications are disclosed in the commonly assigned and concurrently filed U.S. patent application titled "Dental aligner for providing accurate dental treatment" by Liu et al and U.S. patent application titled "Producing wrinkled dental aligner for dental treatment" by Liu et al., the disclosures of which are herein incorporated by reference.

The mold for making the disposable aligner can be kept at the orthodontist's office. Additional disposable aligners can be easily made whenever more copies are needed. In another aspect, the mold can be sent to the clinic or to the patient's home where the disposable dental aligners can be made conveniently without the intervention of the orthodontist.

The disposable aligners can be made of materials that possess the following general properties: the ease to be molded, the capability to be extruded into films or filament, enough hardness to prevent breakage, flexibility, relatively high melting temperature to stand mild heat, strong enough to resist deformation, pliability, and food-grade that is safe for oral use. Preferably, the material is transparent. Examples of materials for disposable dental aligners include acrylic and polycarbonate.

The conventional aligners are usually worn for a period of approximately two weeks. The material properties are optimized to allow it to last for two weeks without breaking. The material properties of the disposable aligner are optimized to be just hard enough to last for just one or two days before it is discarded.

In another embodiment, the disposable dental aligners for a treatment step can comprise slightly different materials. The disposable aligner to be worn at the earlier time of a treatment step can be made of relatively softer material so that the patient can comfortably wear them without feeling much pressure to initiate the teeth movement at the particular treatment step. For instance, the patient may wear the first disposable dental aligner for two days and switch to another disposable dental aligner with increasing hardness. The latter aligners can help to reinforce and solidify the initial movement achieved until the desired full-step movement is achieved.

Although specific embodiments of the present invention have been illustrated in the accompanying drawings and described in the foregoing detailed description, it will be understood that the invention is not limited to the particular embodiments described herein, but is capable of numerous rearrangements, modifications, and substitutions without departing from the scope of the invention. The following claims are intended to encompass all such modifications.

What is claimed is:

1. A method for treating a patient's teeth, comprising:
  receiving an initial configuration of the patient's teeth;
  determining a final configuration of the patient's teeth;
  designing a movement path for at least one of the patient's teeth from the initial configuration toward the final configuration;
  dividing the movement path into a plurality of successive treatment steps, each having a target configuration for the one of the patient's teeth;
  receiving a profile for the patient, the profile comprising at least one of a number of meals, a sleeping pattern, a dental hygiene level, or whether the patient is a smoker; and
  producing two or more redundant disposable dental aligners for each of at least one of the treatment steps to move the one of the patient's teeth to the target configuration, wherein the number of aligners produced for each of the at least one of the treatment steps is selected at least partially in response to the patient's profile, wherein the profile comprising one or more lifestyle factors selected from the patient's eating habits, sleeping pattern, dental hygiene and smoking habits;
  wherein the two or more produced aligners for each of the at least one treatment steps are delivered to the patient at one time and have a material property optimized for usage of a limited duration of not longer than one week, and
  wherein the two or more redundant disposable aligners for each of the at least one treatment steps are aligners of substantially identical shape.

2. The method of claim 1, further comprising producing one or more additional dental aligners of identical shape for one of the treatment steps, wherein the one or more additional dental aligners comprise different material compositions.

3. The method of claim 1, wherein the two or more redundant dental aligners for one of the treatment steps comprise acrylic or polycarbonate.

4. The method of claim 1, further comprising:
  non-simultaneously wearing the two or more redundant dental aligners to move the patient's teeth to the target configuration.

5. The method of claim 4, wherein the redundant disposable dental aligners have a material property optimized for usage of a limited duration of not longer than three days.

6. The method of claim 4, wherein the redundant disposable dental aligners have a material property optimized for usage of a limited duration of not longer than one day.

7. The method of claim 1, further comprising:
  molding the two or more dental aligners using a same mold in a casting chamber.

8. The method of claim 1, further comprising:
  simulating the redundant disposable dental aligners needed for the target configuration at the treatment steps using a digital aligner model; and
  producing the two or more redundant disposable dental aligners in accordance with the digital aligner model.

9. The method of claim 1, wherein the two or more redundant disposable dental aligners are produced with wrinkled surfaces.

10. The method of claim 1, wherein the redundant disposable dental aligners are provided for two or more of the plurality of successive treatment steps.

11. The method of claim 1, wherein the redundant disposable dental aligners are provided for all of the plurality of successive treatment steps.

12. A method for treating a patient's teeth, comprising:
  determining a target configuration for the patient's teeth;
  receiving a profile for the patient, the profile comprising patient lifestyle information;
  selecting a number of redundant dental aligners configured to move the patient's teeth to the target configuration, wherein the number is selected in response to the patient lifestyle information of the received profile;
  producing a plurality of the redundant dental aligners configured to move the patient's teeth to the target configuration, wherein the dental aligners have a material property optimized for usage of a limited duration of not longer than one week; and
  from the plurality of redundant dental aligners, exchanging a new dental aligner for a currently worn dental aligner at a frequency selected in response to the lifestyle information of the patient's profile, wherein the lifestyle information is selected from the patient's eating habits, sleeping pattern, dental hygiene and smoking habits,
  wherein the redundant dental aligners are aligners of substantially identical shape.

13. The method of claim 12, further comprising producing one or more additional aligners of identical shape, wherein the one or more additional dental aligners comprise different material compositions.

14. The method of claim 12, wherein the redundant dental aligners comprise acrylic or polycarbonate.

15. The method of claim 12, wherein the redundant dental aligners have a material property optimized for usage of a limited duration of not longer than three days.

16. The method of claim 12, further comprising:
  molding the plurality of redundant dental aligners using a same mold in a casting chamber.

17. The method of claim 12, wherein the plurality of dental aligners are produced with wrinkled surfaces.

18. A system for treating a patient's teeth, comprising:
  a computer configured to generate a target configuration for the patient's teeth and a quantity of redundant dental aligners to be produced for said target configuration, wherein a material property of the redundant dental aligners is optimized for usage of a limited duration, and wherein the quantity of redundant aligners to be produced is generated at least partially in response to a profile for the patient, the patient's profile comprising one or more lifestyle factors selected from the patient's eating habits, sleeping pattern, dental hygiene and smoking habits; and an apparatus configured to produce a plurality of redundant dental aligners configured to move the patient's teeth toward the target configuration;

wherein the redundant dental aligners are aligners of substantially identical shape.

19. The system of claim 18, wherein the redundant dental aligners comprise acrylic or polycarbonate.

20. The system of claim 18, wherein the apparatus is configured to mold the redundant dental aligners using a same mold in a casting chamber.

21. A method for treating a patient's teeth, comprising:

receiving a target configuration of a patient's teeth;

receiving a profile for the patient, the profile comprising one or more lifestyle factors;

generating a frequency for changing disposable dental aligners based at least partially on the patient's profile, wherein the profile comprising one or more lifestyle factors selected from the patient's eating habits, sleeping pattern, dental hygiene and smoking habits;

optimizing a material property of the dental aligners for usage of a limited duration; and providing a plurality of redundant disposable dental aligners to move said patient's teeth from an initial configuration to said target configuration, wherein the redundant disposable dental aligners are aligners of substantially identical shape.

* * * * *